US011696870B2

(12) United States Patent
Peguero et al.

(10) Patent No.: US 11,696,870 B2
(45) Date of Patent: Jul. 11, 2023

(54) MEDICAL GEL WARMING SYSTEMS AND METHODS

(71) Applicant: NEXT Medical Products Company, Branchburg, NJ (US)

(72) Inventors: Sergio Peguero, Flemington, NJ (US); Nickolas P. Demas, Branchburg, NJ (US)

(73) Assignee: Next Medical Products Company, Branchburg, NJ (US)

( * ) Notice: Subject to any disclaimer, the term of this patent is extended or adjusted under 35 U.S.C. 154(b) by 513 days.

(21) Appl. No.: 16/783,751

(22) Filed: Feb. 6, 2020

(65) Prior Publication Data

US 2020/0253825 A1 Aug. 13, 2020

Related U.S. Application Data

(60) Provisional application No. 62/802,464, filed on Feb. 7, 2019.

(51) Int. Cl.
*A61J 1/16* (2023.01)
*A61B 8/00* (2006.01)
*A61M 5/44* (2006.01)

(52) U.S. Cl.
CPC .............. *A61J 1/16* (2013.01); *A61B 8/4281* (2013.01); *A61M 5/445* (2013.01); *A61J 2200/42* (2013.01)

(58) Field of Classification Search
CPC ... A61M 5/445; H05B 1/0269; H05B 1/1025; A47J 36/2433; A47J 2200/42; A61F 7/0085; A61F 1/16
See application file for complete search history.

(56) References Cited

U.S. PATENT DOCUMENTS

| 4,215,267 | A | * | 7/1980 | Kaebitzsch | ........... A47J 27/004 219/453.11 |
| 4,555,478 | A | * | 11/1985 | Reczek | .............. G03C 7/30547 430/222 |
| 5,170,344 | A | * | 12/1992 | Berton | ............... G05B 19/0426 62/135 |
| 5,568,810 | A | * | 10/1996 | Hamers | ................ A61B 8/4281 128/898 |
| 2003/0000939 | A1 | * | 1/2003 | Faries, Jr. | ............. A61M 5/445 219/508 |
| 2014/0231406 | A1 | * | 8/2014 | Tsang | ...................... A61M 5/44 219/394 |
| 2019/0076118 | A1 | * | 3/2019 | Dohm | ................... A61F 7/0241 |

* cited by examiner

*Primary Examiner* — Timothy R Waggoner
(74) *Attorney, Agent, or Firm* — Dorsey & Whitney LLP (57) ABSTRACT

A warming device and system for warming medical gel to a comfortable temperature prior to application to a patient. A warming chamber configured to receive one or more gel containers (e.g., packets or bottles) disposed in a horizontal orientation with a cover sealing the chamber. Multiple protrusions and/or depressions disposed on an inside surface of the chamber can be used to soften thermal conduction of heat to the gel containers and inhibit hot spots. A flexible heating element and an intermediate thermal conducting member can extend up one or more sides of the warming chamber. Multiple buttons can be used to set different gel temperature settings.

20 Claims, 5 Drawing Sheets

MEDICAL GEL WARMING SYSTEMS AND METHODS

RELATED APPLICATIONS

This application claims priority to U.S. Provisional Application No. 62/802,464, filed on Feb. 7, 2019 and titled, "MEDICAL GEL WARMING SYSTEMS AND METHODS," which is herein incorporated by reference in its entirety.

TECHNICAL FIELD

The present disclosure relates generally to warming systems and receptacles. More specifically, the present disclosure relates to devices, systems, and methods for warming ultrasound gel packets or bottles.

BRIEF DESCRIPTION OF THE DRAWINGS

The embodiments disclosed herein will become more fully apparent from the following description and appended claims, taken in conjunction with the accompanying drawings. The drawings depict only typical embodiments, which will be described with additional specificity and detail through use of the accompanying drawings in which:

DETAILED DESCRIPTION

Many medical procedures include the application of topical gels to the skin of a patient. The current disclosure relates to such gels, which include, but are not limited to, gels used during an ultrasound imaging procedure. The gels may be stored inside a hospital or other medical facility where the temperature of the gels may substantially assume the ambient temperature of the storage area, which temperature may commonly be about 72 degrees Fahrenheit (F.). Typical body temperature is about 98 degrees F. Many patients may find it uncomfortable to have a gel at about 72 degrees F. applied to their skin. The comfort of a patient may be enhanced by warming the gel to a temperature close to or slightly greater than typical body temperature. Placing and storing gels in a warmed environment before application would provide warmed gels at the time of application. The gels may be packaged in containers, such as soft flexible packets (e.g., such as packets having volume capacities between about 10 and about 50 ml) or they may be packaged in bottles (e.g., such as bottles having gel capacities of about 4 to about 10 ounces). The gel bottles may be cylindrical in shape. Other types of containers can also be used.

The following disclosure describes a warming system configured to receive containers of gel (e.g., packets or bottles) in a warming chamber. The warming chamber can be configured to have an internal temperature at or close to the desired temperature for comfortable application to a patient. The warming system may comprise safety systems to ensure that the warming chamber does not heat the gel to a temperature to cause discomfort or injury to a patient. The warming system may obtain electrical energy, such as through one or more batteries or through a corded connection to a facility electrical receptacle. The warming system may be configured to be energized (e.g., plugged in and/or turned on) for extended periods of time. In some instances, gel containers may be placed in the chamber and warmed thereby for up to several days or more. In other instances, gel containers may be placed or stored in the chamber while the gel warming system is de-energized (e.g., turned off) after which the user may turn on the gel warming system at their discretion and allow the gel to warm up for a period of time prior to use. The gel warming system may be configured to warm the gel in a relatively short period of time without overheating the gel. The warming system may be sized and configured for placement at or adjacent the point of use, for example adjacent an ultrasound imaging machine, so that the gel may be used immediately after being warmed, before the gel cools down. In such instances, a user may access the gel with one hand while performing another process with the other hand.

It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, electrical, magnetic, electromagnetic, fluid, and thermal interaction. Thus, two components may be coupled to each other even though they are not in direct contact with each other. For example, two components may be coupled to one another through an intermediate component.

Various features are sometimes grouped together in a single embodiment, figure, or description thereof for the purpose of streamlining the disclosure. Many of these features may be used alone and/or in combination with one another. Additional aspects and advantages will be apparent from the following detailed description of embodiments, which proceeds with reference to the accompanying drawings.

Figure 1:
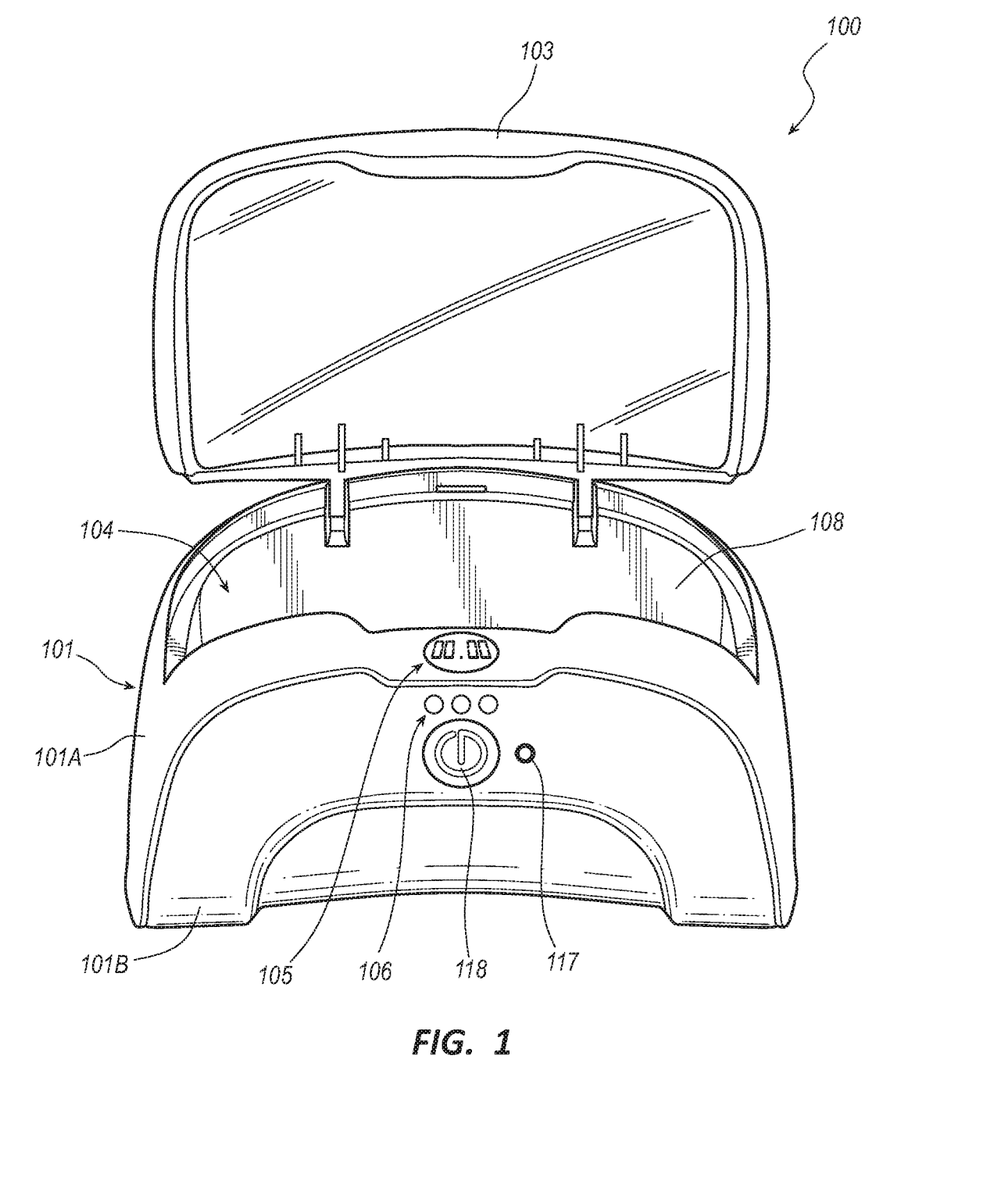
FIG. 1 is a front perspective view of an embodiment of a gel warming system.
Figure 2:
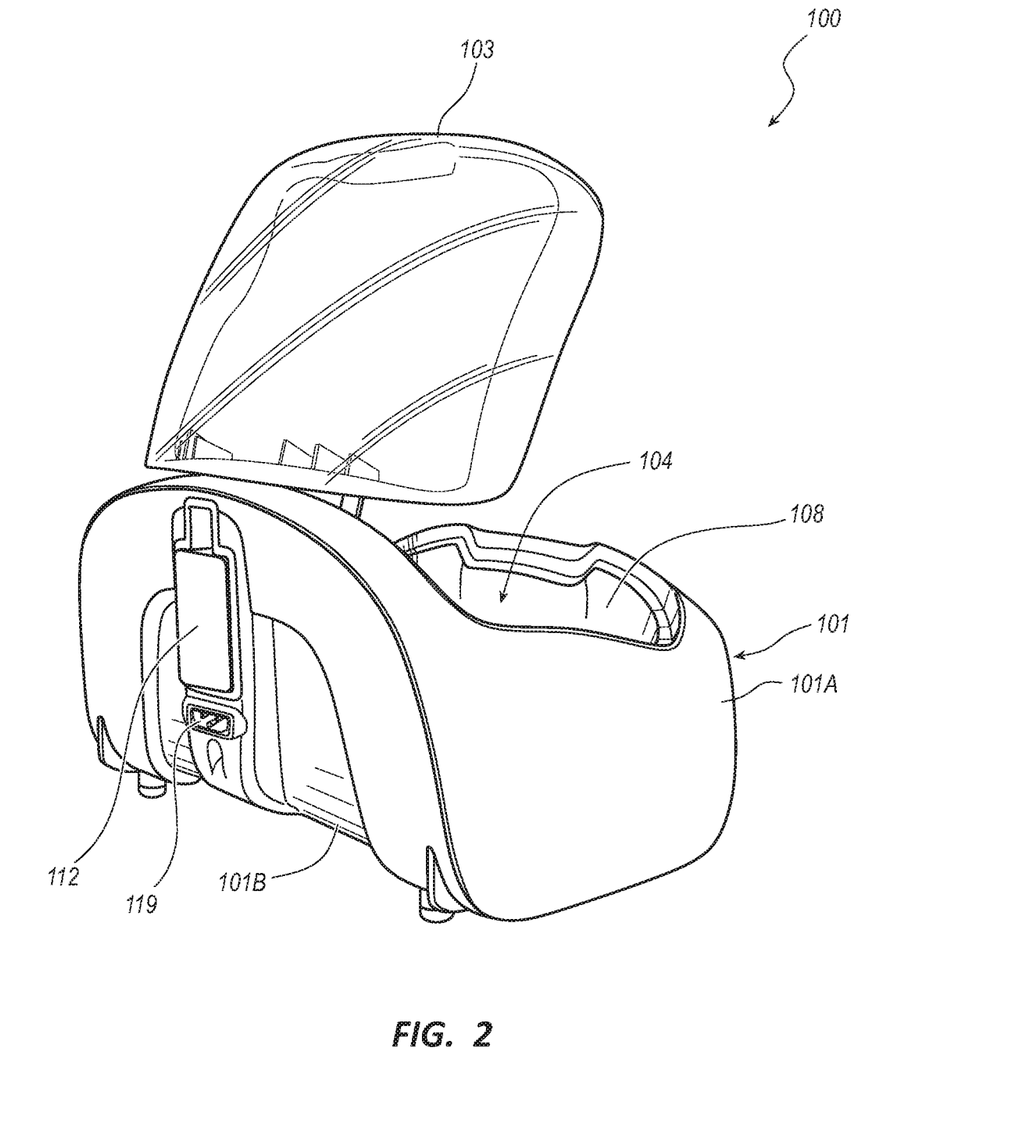
FIG. 2 is a rear perspective view of the gel warming system of FIG. 1.
Figure 3:
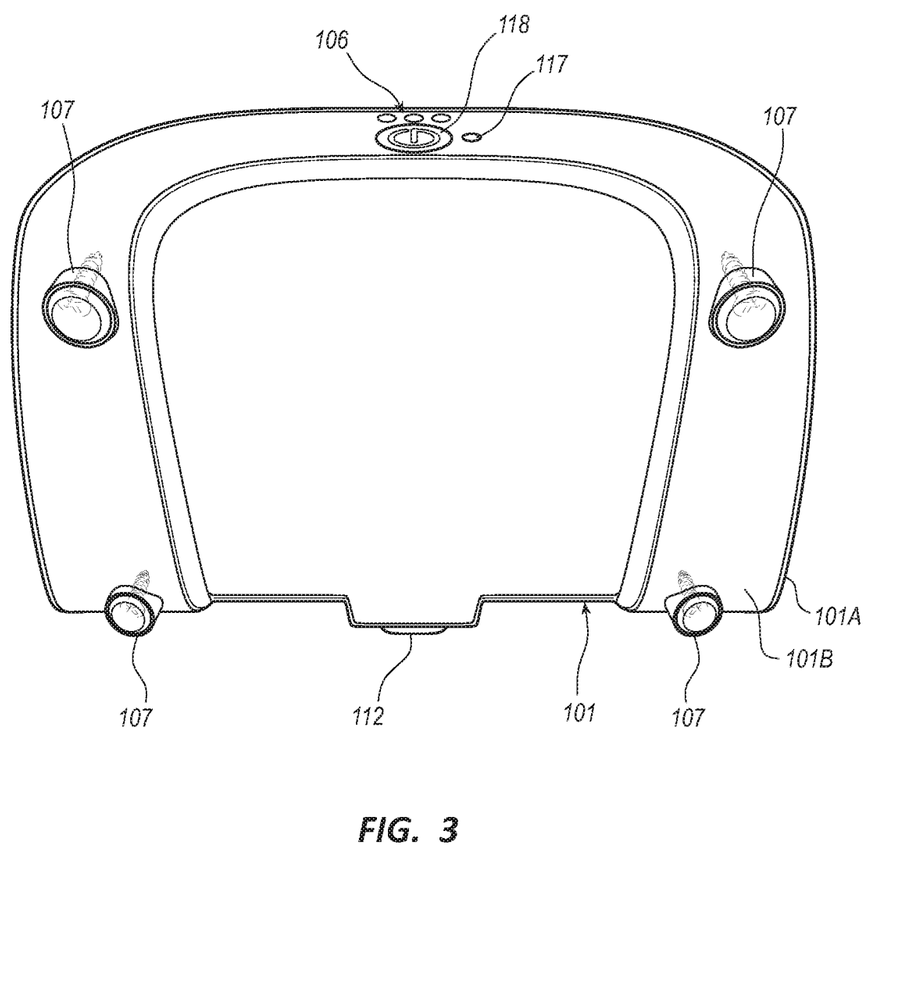
FIG. 3 is a bottom view of the gel warming system of FIG. 1.

Referring to FIGS. 1-3 which depict various views of the medical gel warming system 100. The medical gel warming system 100 may comprise a housing 101 configured to contain functional portions and components of the medical gel warming system 100. The housing 101 may provide a structural framework to which components are attached. The housing 101 may be manufactured of a polymeric or plastic material suitable for high-volume repeatable manufacturing processes such as injection molding. The external surface of the housing 101 may facilitate one or more of the aesthetic appearance, ergonomic handling, ease of cleaning and/or disinfecting, electrical shock prevention, etc. The housing 101 may also comprise thermal insulative properties to inhibit the ambient temperature from substantially affecting the temperature control process, prevent external surfaces from becoming too hot to touch, and/or minimize energy waste, etc. The shape and/or size of the housing 101 can vary. In some embodiments, the shape may comprise external dimensions between about 7 and about 10 inches side to side, between about 6 and about 8 inches front to back, and between about 6 and about 9 inches top to bottom. The housing 101 may comprise one or more operating interface components coupled to the housing 101, such as push buttons 106, an information display 105, an on-off switch 118, and an indicator light 117, as are further described below. The top of the housing 101 may comprise an opening 104 to provide access to a warming chamber 108 for placement and retrieval of gel containers into and out of the warming chamber 108.

The housing 101 may comprise a top portion 101A and a bottom portion 101B coupled together using fasteners such as screws. The top and bottom portions 101A, 101B, when coupled together, may prevent various hazards to the user, such as burns or electrical shock. Separation of the top and bottom portions 101A, 101B of the housing 101 may provide access to internal components as needed for service and/or repair. The fasteners may be located on a bottom surface of the bottom portion 101B of the housing 101 so as to not be visible when the medical gel warming system 100 is placed on a horizontal surface, such as a desk, table, or cart.

As shown in FIG. 3, in some embodiments, the housing 101 comprises one or more legs or feet 107. In certain embodiments, the housing 101 may comprise three, four, or more legs or feet 107. The legs or feet 107 may be configured to provide for stable placement of the medical gel warming system 100 on a horizontal surface such as a desk, table, or cart. The legs or feet 107 can be individually adjustable to level the medical gel warming system 100 on the horizontal surface. The legs or feet 107 may also comprise a portion formed of an elastomeric material consistent with providing a frictional coupling to the horizontal surface so as to prevent inadvertent sliding of the medical gel warming system 100 on the horizontal surface. The legs or feet 107 may be coupled to a bottom surface of the bottom portion 101B of the housing 101, such as using mechanical fasteners (e.g., screws), pressure fit engagements, or adhesives. In some embodiments, the legs or feet 107 may also be positioned to cover and/or hide the fasteners that are used to couple the top and bottom portions 101A, 101B of the housing together. Covering the fasteners with the legs or feet 107 may inhibit or prevent tampering with the internal components of the medical gel warming system 100 and/or indicate if tampering as taken place. For instance, removal of a leg or foot 107 that was adhesively attached may indicate tampering.

Disposed at least partially within the housing 101 is the warming chamber 108. The warming chamber 108 defines a cavity and is configured to receive or otherwise facilitate placement of one or more gel containers (e.g., packets and/or bottles) therein. In some embodiments, the warming chamber 108 may be configured to receive gel bottles, which may be cylindrical. In such instances, the warming chamber 108 may be configured to receive the gel bottles in a horizontal position, i.e., with the bottles lying on their sides. If desired, the warming chamber 108 can also be sized to receive gel bottles in a vertical position. In certain embodiments, the warming chamber 108, with the cover 103 closed, can be configured to receive at least one bottle having a gel capacity of at least eight ounces or more. In certain embodiments, the warming chamber 108, with the cover 103 closed, may be sized to accommodate three or more bottles of gel, each bottle having a gel capacity of at least eight ounces or more.

The size and/or shape of the warming chamber 108 can vary. In some embodiments, the warming chamber 108 may comprise an approximately rectangular shape having a bottom wall, two side walls, and two end walls. The opposing side and end walls may or may not be parallel. The internal shape of the warming chamber 108 may facilitate a desired thermal coupling of the chamber walls with the gel containers. Internal corners may comprise internal radii which may be sized to provide enhanced surface contact between the gel containers and the chamber walls and thereby provide a desired thermal coupling to the gel containers. Such internal radii may also facilitate cleaning of the internal chamber surfaces.

The internal surfaces of the chamber walls may comprise features to establish the desired thermal coupling of the chamber walls to the gel containers. In some embodiments, highly intimate thermal coupling may be desired so as to maximize heat transfer from the chamber walls to the gel containers. In other embodiments, a less intimate thermal coupling may be desirable so as to prevent hot spots (overheating of gel portions). In some embodiments, the chamber walls may comprise surface features 109 (See FIG. 4) to prevent hot spots. Such surface features 109 may include a plurality of protrusions and/or depressions such as bumps, ridges, troughs, etc. The surface features 109 may facilitate air flow between the chamber walls and the gel containers. The warming chamber 108 may be formed of injected molded plastic such as polypropylene. A top edge of the side and end walls of the warming chamber 108 may align with and be sealably coupled to a top edge of the housing 101.

The medical gel warming system 100 comprises a cover 103 which may be hingedly coupled to the housing 101. The cover 103 may be configured to provide a thermal barrier between the warming chamber 108 and the external environment when the cover 103 is closed. When closed, the cover 103 may form a seal with the warming chamber 108 so as to inhibit and/or minimize air flow into and/or out of the chamber 108. The cover 103 may be at least partially formed of a transparent or translucent material to facilitate visual observation of the contents of the warming chamber 108 when the cover 103 is closed. The hinged coupling may comprise features to facilitate enhanced operation, such as friction, detents, rotational stops, latches, etc. The cover 103 may be configured for one handed opening and closing. In some instances, a user may need to hold a probe or other device with one hand while accessing gel from the chamber 108 with the other hand. As shown in FIG. 2, in some embodiments, a power supply 112 and a plug 119 may be disposed on a back side of the medical gel warming system 100. In other embodiments, a compartment for batteries can also be included in addition to or in place of the power supply and/or plug 119. Rechargeable or non-rechargeable battery components can be used.

Figure 4:
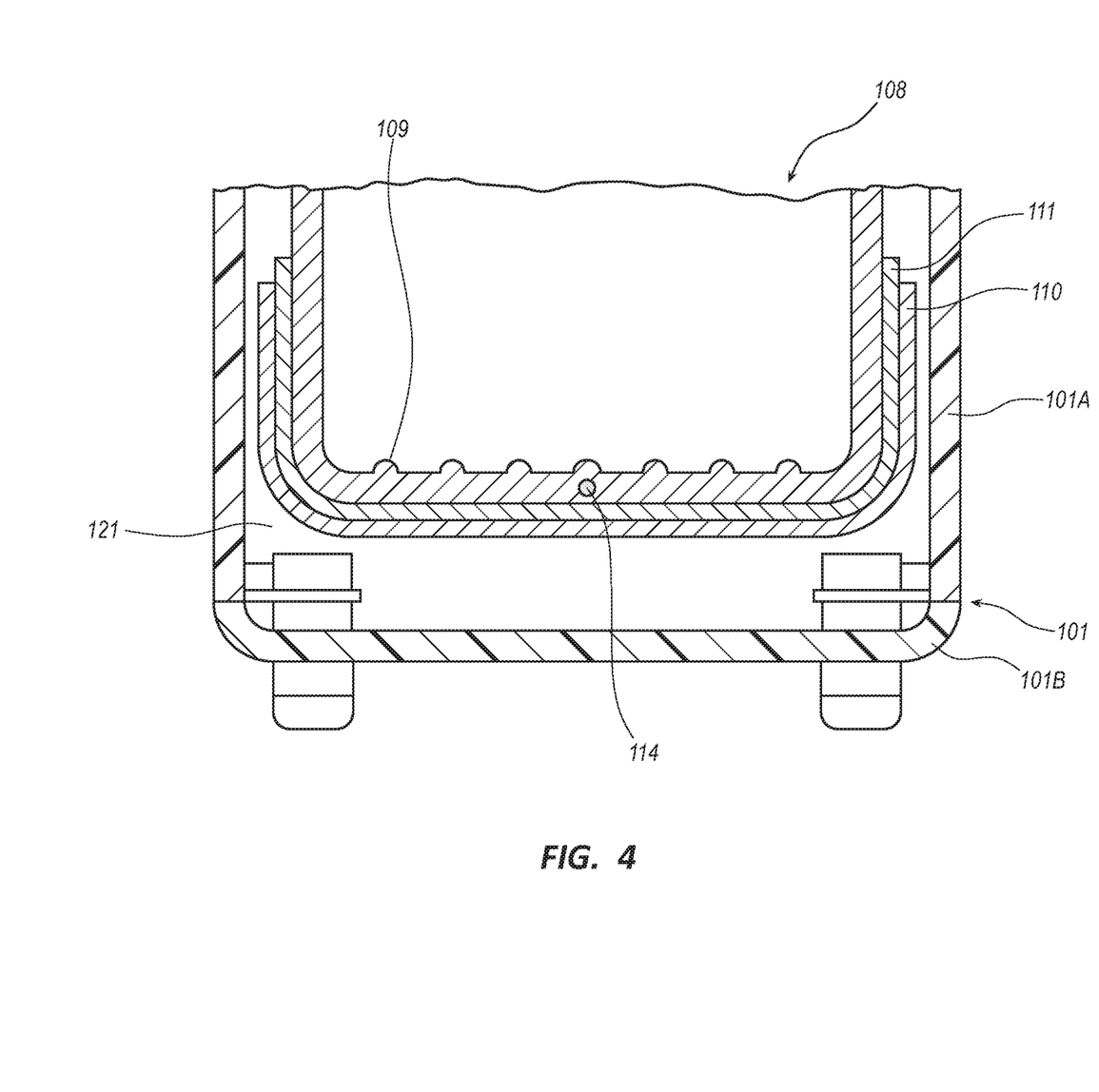
FIG. 4 is a partial cross-sectional side view of the gel warming system of FIG. 1.

Referring to FIG. 4, the medical gel warming system 100 may comprise a heating element 110 for providing heat to the chamber 108 and the gel disposed therein. The heating element 110 may comprise a flexible film having a defined heating area. In some embodiments, the heating element 110 comprises polyethylene. Other materials can also be used. The heating element 110 may be thermally coupled to the warming chamber 108. In some embodiments, the heating element 110 is thermally coupled to an intermediate thermal coupling member 111, which in turn may be thermally coupled to an external or outwardly facing surface of one or more walls of the chamber 108. In other embodiments, the heating element 110 may be thermally coupled directly to one or more chamber walls. The heating element 110 and the intermediate thermal coupling member 111 may extend across the bottom wall of the chamber 108 and may also extend upward along one or more side and/or end walls of the chamber 108 so as to cover a large portion of the exterior or outwardly facing surfaces of the chamber 108. The intermediate thermal coupling member 111 may be configured to facilitate a substantially uniform transfer of heat between the heating element 110 and the chamber walls. The intermediate thermal coupling member 111 may also comprise a thermal mass configured to store heat energy. The intermediate thermal coupling member 111 may comprise aluminum or otherwise be formed of an aluminum plate. The aluminum plate may be coupled to the walls of the warming chamber 108, such as via an adhesive with enhanced thermal coupling properties. Other types of conductive materials and/or conductive metals can also be used as the intermediate thermal coupling member. The intermediate thermal coupling member 111 may provide for a distribution of heat over a larger area than the heating element 110. In other words, in instances when the area of a heating element 110 is less than the area of the intermediate thermal coupling member 111, the intermediate thermal coupling member 111 may conduct heat laterally and/or beyond the outer perimeter of the heating element 110. The intermediate thermal coupling member 111 may also provide for a more constant transfer of heat to the warming chamber 108 within the perimeter of the heating element 110. The heating element 110 may be coupled to the intermediate thermal coupling member 111, such as via an adhesive with enhanced thermal coupling properties. In other embodiments, the intermediate thermal coupling member 111 may be coupled to the heating element 110 opposite the walls of the warming chamber 108. In other words, the heating element 110 may be disposed between the intermediate thermal coupling member 111 and the chamber walls. Other methods of coupling the heating element 110, the intermediate thermal coupling member 111, and the heated walls of the warming chamber 108 to each other are included in this disclosure, such as clamping, integral molding, etc.

The warming chamber 108 may also comprise a temperature sensor 114. The temperature sensor 114 may be configured to measure and/or detect a temperature, and then provide a corresponding temperature signal to a temperature controller. For instance, the temperature sensor 114 may be configured to measure and/or indicate a temperature of the warming chamber 108. This measured temperature can also represent and/or indicate an approximate temperature of the gel within the warming chamber 108. The temperature sensor 114 can then relay a corresponding temperature signal to the temperature controller. In some instances, the temperature sensor 114 may be disposed at a location so as to measure the temperature of a portion of a chamber wall of the warming chamber 108. The location of the temperature sensor 114 may be such that thermal conduction between the temperature sensor 114 and the gel within the containers is maximized. The location of the temperature sensor 114 may also be such that thermal conduction between the temperature sensor 114 and the heating element 110 and/or the intermediate thermal coupling member 111 is minimized or otherwise controlled. Such a location of the temperature sensor 114 may facilitate a stable control of the temperature of the gel and minimize temperature overshoot. In some embodiments, location of the temperature sensor 114 may be such that it measures a hotter portion of the warming chamber 108 when the heating element 110 is energized so as to inhibit overheating of the gel or portions thereof. In certain embodiments, a temperature sensor is disposed near or approximately near the center of the warming chamber 108 (e.g., in the middle or the center of the bottom wall of the warming chamber 108). In some embodiments, multiple temperature sensors may be used to measure the temperature at multiple locations of the warming chamber 108.

The warming chamber 108 may be insulated from the effects of ambient temperature. In some embodiments, the housing 101 may comprise thermal insulation materials and/or structure between the side and end walls of the warming chamber 108 and the inside surface of the housing 101. In some embodiments, the housing 101 may comprise thermal insulation materials and/or structure between (a) one or both of the heating element 110 and the intermediate thermal coupling member 111 and (b) the inside surface of the housing 101. In some embodiments, thermal insulation materials and or structure may optimally isolate the temperature sensor 114 from heat sources or ambient temperatures. In some embodiments, the housing 101 may contain a fire resistant insulation 121 disposed between the outside wall of the chamber 108 and the inside wall of the housing 101.

Figure 5:
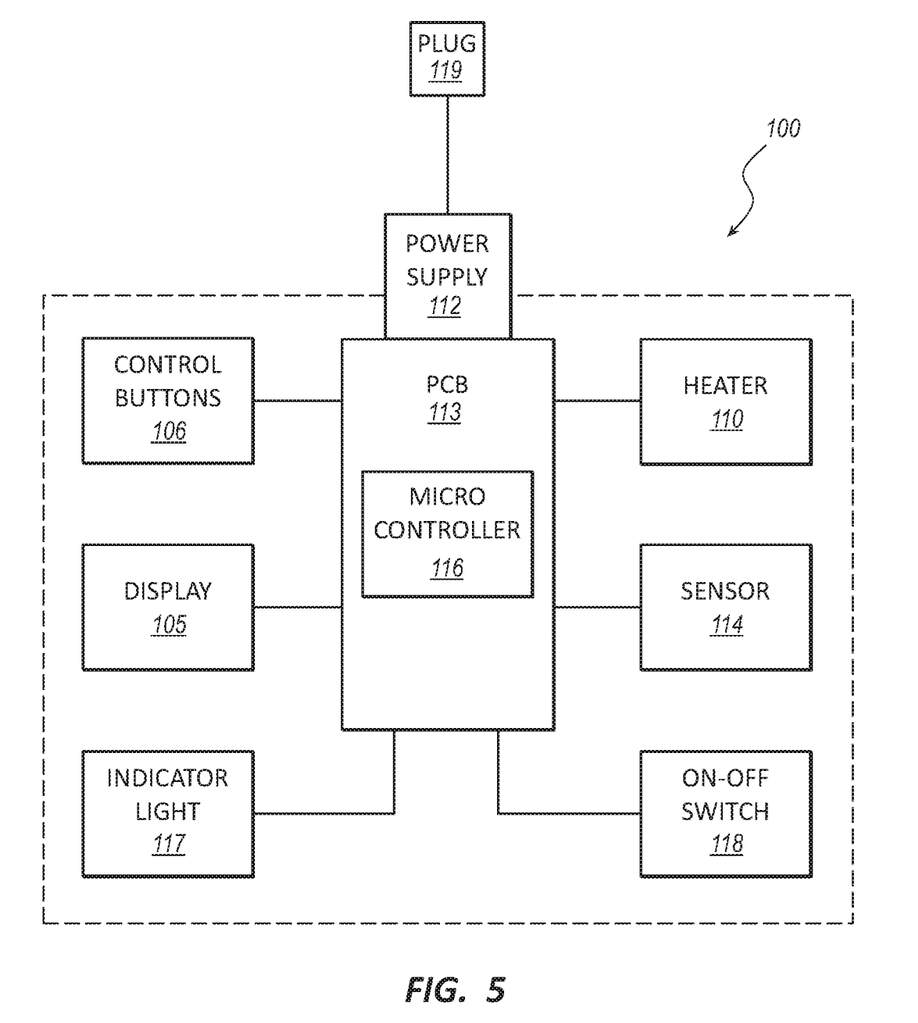
FIG. 5 is a schematic of an electrical system of the gel warming system of FIG. 1.

Referring to FIG. 5, an electrical system of the medical gel warming system 100 may comprise one or more of the plug 119, the power supply 112, the on-off switch 118, the indicator light 117, a printed circuit board 113 including a micro controller 116, the heating element 110, the temperature sensor 114, the operator interface (e.g., buttons 106), and the display 105. A power cord may be provided to connect facility power to the plug 119. In another embodiment, one or more batteries (rechargeable or non-rechargeable batteries) can be used as the power source. Various wires and connectors may couple the electronic components to each other. The heating element 110, the temperature sensor 114, and the micro controller 116 including software may combine to form a temperature controller. In some embodiments, the temperature controller can be configured to modulate the temperature of the warming chamber. For instance, the temperature controller can be configured to establish and maintain a temperature in the warming chamber 108 as indicated by the temperature sensor 114 in accordance with a desired gel temperature setting. Each of the electronic components is further described below.

The power supply 112 may perform several functions. The power supply 112 may automatically accommodate a range of input voltage parameters to accommodate use of the medical gel warming system 100 in several countries and may convert the input voltage to 12 volts DC (direct current). The power supply 112 may limit radiated and conducted electromagnetic interference to comply with electrical safety standards and may provide immunity from power source disturbances. The power supply 112 may be disposed within a cutout of the housing wall as shown in FIG. 2, so as to place at least a portion of the power supply 112 in an ambient environment rather than a heated environment inside the housing 101. Keeping the power supply 112 cooler may enhance reliability of the power supply 112. Placement of at least a portion of the power supply 112 outside of the housing 101 also may inhibit heat generated by the power supply 112 from substantially affecting the temperature control process. Portions of the power supply 112 may also be disposed inside the housing 101. The power supply 112 may comprise the specifications as shown in the table below for model # IMR-30-12.

| MODEL | | IRM-30-5 | IRM-30-12 | IRM-30-15 | IRM-30-24 | IRM-30-48 |
|---|---|---|---|---|---|---|
| OUTPUT | DC VOLTAGE | 5 V | 12 V | 15 V | 24 V | 48 V |
| | RATED CURRENT | 6 A | 2.5 A | 2 A | 1.3 A | 0.63 A |
| | CURRENT RANGE | 0-6 A | 0-2.5 A | 0-2 A | 0-1.3 A | 0-0.63 A |
| | RATED POWER | 30 W | 30 W | 30 W | 31.2 W | 30.2 W |
| | RIPPLE & NOISE (max) Note 2 | 120 mVp-p | 150 mVp-p | 200 mVp-p | 240 mVp-p | 300 mVp-p |
| | VOLTAGE TOLERANCE Note 3 | ±2.5% | ±2.5% | ±2.5% | ±2.5% | ±2.5% |
| | LINE REGULATION | ±0.5% | ±0.5% | ±0.5% | ±0.5% | ±2.5% |
| | LOAD REGULATION | ±1.0% | ±0.5% | ±0.5% | ±0.5% | ±0.5% |
| | SETUP, RISE TIME | | 1000 ms, 30 ms/230 VAC 1500 ms, 30 ms/115 VAC at fullload | | | |
| | HOLD UP TIME (typ.) | | 40 ms/230 VAC 12 ms/115 VAC at full load | | | |
| INPUT | VOLTAGE RANGE | | 85-264 VAC | | | |
| | FREQUENCY RANGE | | 47-440 Hz | | | |
| | EFFICIENCY (Typ.) | 83% | 88% | 88% | 88.5% | 90% |
| | AC CURRENT (Typ.) | | 0.75 A/115 VAC 0.5 A/230 VAC | | | |
| | INRUSH CURRENT (Typ.) | | COLD START 25 A/115 VAC 45 A/230 VAC | | | |
| | LEAKAGE CURRENT | | <0.25 mA/240 VAC | | | |
| PROTECTION | OVERLOAD | | 105%-160% rated output power Protection type: Hiccup mode, recovers automatically afterfault condition is removed | | | |
| | OVER VOLTAGE | 6.25-6.75 V | 12.5-16.2 V | 15.75-20.25 V | 25.2-32.4 V | 50.4-64 V |
| | | | Protection type: Shut off o/p voltage, clamping by zener diode | | | |
| ENVIRONMENT | WORKING TEMP. | | −30 ~ +70° C. (Refer to "Derating Curve") | | | |
| | WORKING HUMIDITY | | 20-90% RH non-condensing | | | |
| | STORAGE TEMP. HUMIDITY | | −40-+85° C., 10-95% RH | | | |
| | TEMP. COEFFICIENT | | ±0.03%/° C. (0-50° C.) | | | |
| | VIBRATION | | 10-500 Hz, 5G 10 min./1 cycle period for 60 min. each along X,Y, Z axes | | | |
| SAFTY & EMC | SAFETY STANDARDS | | UL60950-1, TUV EN60950-1, EAC TP TC 004 approved | | | |
| | WITHSTAND VOLTAGE | | I/P-O/P: 3 KVAC | | | |
| | ISOLATION RESISTANCE | | I/P-O/P: 100M Ohms/500 VDC/25° C./70% RH | | | |
| | EMC EMISSION | | Compliance to EN55032 (CISPR32) Class B, EN61000-3-2-3, EAC TPTC 020 | | | |
| | ENC IMMUNITY | | Compliance to EN61000-4-2, 3, 4, 5, 6, 8, 11, EN55024, heavy industry level (surge L-N: 1 KV), criteria A, EAC TP TC 020 | | | |
| OTHERS | MTBF | | 593.3K hrs min. MIL-HDBK-217F (25° C.) | | | |
| | DIMENSION | | PCB mounting style: 69.5 * 39 * 24 mm (L * W * H) Screw terminalstyle: 91 * 39.5 * 28.5 mm (L * W * H) | | | |
| | PACKING | | PCB mounting style: 0.094 Kg: 144 pcs/14.5 Kg/0.97 CUFT Screw terminal style: 0.113 Kg: 120 pcs/14.6 Kg/0.74 CUFT | | | |

Other types of power supplies 112 having other specifications can also be used. As previously discussed, in some embodiments the power supply is configured to accommodate one or more batteries (rechargeable or non-rechargeable batteries) as the power source.

The on-off switch 118 facilitates energizing and de-energizing of the medical gel warming system 100, and the indicator light 117 may visually communicate to the user the energized and de-energized status. The on-off switch 118 and the indicator light 117 may be electrically coupled to the micro controller 116. The indicator light 117 may also indicate a status of the temperature of the warming chamber 108 (and/or gel contained therein) as sensed by the temperature sensor 114 during the warming process. For example, the indictor light 117 may blink when the temperature of the warming chamber 108 (and/or gel contained therein) is below a desired temperature setting such as when the medical gel warming system 100 is initially turned on. The indictor light 117 may be disposed in a continuously "on" state when the temperature of the warming chamber 108 (and/or gel contained therein) has reached the desired temperature setting, or vice versa. In other embodiments, the indicator light 117 can be configured to change colors to indicate the status of the temperature of the warming chamber 108 (and/or gel contained therein). Other types of indicator light configurations can also be used.

The printed circuit board 113 may comprise several operating functions, such as taking input from the operator interface (e.g., buttons 106) and the temperature sensor 114 and providing output to the display 105 and the heating element 110. The printed circuit board 113 can also comprise a micro controller configured to store and run a software program.

The operator interface can be configured in various ways. For instance, the operator interface can be digital and/or can include one or more buttons 106. In some embodiments, the operator interface can include one or more push buttons 106 that may facilitate operator input. In the depicted embodiment, three buttons 106 are provided, but more or less buttons 106 can also be used. In one operating mode, pressing each button 106 may define a specified temperature or warmer chamber setting. For example, the one or more buttons 106 may establish one or more temperature or warmer chamber settings. For example, the one or more buttons 106 (e.g., three buttons) may each comprise a predefined temperature setting, such as about 95, about 100, or about 105 degrees F. The one or more buttons 106 may also be programed by the user to re-define the temperature or warmer chamber settings to be different than about 95, about 100, or about 105 degrees F. The micro controller 116 may, for safety reasons, also be configured to limit the temperature or warmer chamber to 105 degrees F. or below as measured by the temperature sensor 114. One or more of the buttons 106 may also define a default temperature or warmer chamber setting wherein upon energizing (turning on) the medical gel warming system 100, the temperature controller establishes and maintains the temperature of the warmer chamber (and/or gel contained therein) at the default temperature setting. In one embodiment, the default temperature setting may be a temperature of between about 80 and about 105 degrees F., between about 90 and about 105 degrees F., or between about 95 and about 105 degrees F. In some instances, the one or more buttons 106 may perform other functions, such as changing modes, entering programmable values, changing displayed information, resetting error codes, confirming input, etc.

The display 105 provides information to the operator. In some embodiments, the display 105 comprises three characters having seven segments each. In other embodiments, the display 105 may comprise additional display capability such as more than three characters. Other types of displays 105 can also be used. The display 105 may provide information to the operator, such as the temperature setting, the current temperature of the warming chamber as measured by the temperature sensor 114, an adjusted or filtered temperature value, error codes, mode of operation, programmable settings, on-off status, alarms, etc. The micro controller 116 may be programmed to display temperatures in Fahrenheit or Celsius.

The heating element 110 converts electrical energy to heat. For instance, the heating element 110 can convert electrical energy from the power supply into heat. In some embodiments, the heating element 110 is a resistive element configured to operate on 12 volts DC. The heating element 110 may be configured to provide an abundance of heat energy when energized with electrical energy (such as 12 volts). The abundance of heat energy may facilitate a short warming-up period of the warming chamber 108 and/or the gel contained therein, such as when the medical gel warming system 100 is first turned on. The heating element 110 may also be configured to draw an electrical current within a reliable operating range of the power supply 112 or power source.

The temperature sensor 114 converts a measured temperature value into an electrical signal for input to the micro controller 116. The temperature sensor 114 may be a negative temperature coefficient (NTC) thermistor providing a resistance value that correlates to a measured temperature. In other embodiments, other temperature sensors may be used, such as thermocouples.

The printed circuit board 113 may be configured to comprise and operate under various specifications, including the following illustrative specifications:

Temperature Control Range: −50 to 110 C
Resolution at −9.9 to 99.9 C: 0.1 C
Resolution at All Other Temperatures: 1 C
Measurement Accuracy: 0.1 C
Control Accuracy: 0.1 C
Refresh Rate: 0.5 Seconds
Input Power (DC): 12V
Measuring Inputs: NTC (10K 0.5%)
Waterproof Sensor: 0.5M
Output: 1 Channel
Relay Output, Capacity: 10A
Power Consumption Static Current:<=35 mA
Current:<=65 mA
Environmental Requirements:
 Temperature: −10·60 C
 Humidity: 20-85%
 Dimensions: 48 mm×40 mm×14 mm Other specifications can also be used for the printed circuit board 113.

The medical gel warming system 100 can comprise a temperature control algorithm programmed in software on the micro controller 116. The algorithm in combination with circuitry on the printed circuit board 113 can modulate the electrical energy applied to the heating element. For instance, the algorithm in combination with circuitry on the printed circuit board 113 can be configured to energize and/or de-energize the heating element 110 in response to a temperature measurement or signal from the temperature sensor 114. In some embodiments, the algorithm may operate as follows. The algorithm compares the temperature of the warming chamber (and/or gel contained therein) T1 as measured by the temperature sensor 114 with the desired temperature setting T0 as selected by the user interface (e.g., pressing one of the buttons 106). If T0 is greater than T1 by a defined difference D0, the heating element 110 is energized, and if not the heating element 110 remains de-energized. If T1 is greater than T0 by a defined difference D1, the heating element 110 is de-energized, and if not the heating element 110 remains energized. The defined difference D0 and the defined difference D1 may be the same or different. In some embodiments, the defined difference D0 and D1 are less than about 5, about 4, about 3, about 2, or about 1 degree F.

In some embodiments, other algorithms may be employed to shorten the time to heat the warming chamber (and/or gel contained therein) to the desired temperature, prevent over-temperature swings, etc. Some embodiments comprise an over-temperature safety algorithm which can de-energize the heating element 110 if the temperature of the warming chamber (and/or gel contained therein) T1 exceeds a defined maximum temperature limit T2, which maximum temperature limit may be about 105 degrees F.

In some embodiments, the temperature control algorithm may comprise one or more temperature offsets. A temperature offset may adjust a temperature input value to the algorithm. In some instances, a temperature offset may be applied to the temperature setting T0. For example, the temperature setting T0 may be adjusted by an offset to produce a temperature in the warming chamber (and/or gel contained therein) that is slightly higher than the temperature setting T0 (e.g., about 1, about 2, about 3, about 4, about 5, or more degrees F. higher). This may be advantageous if the warmed gel is not typically used immediately when removed from the chamber 108 and will thus cool down before use. Such may also be the case for a room temperature that is lower than typical. An offset may also be applied to the temperature of the warming chamber (and/or gel contained therein) T1 as measured by the temperature sensor 114. For example, the gel when packaged in flexible packets may warm up to a slightly higher temperature than the gel when packaged in bottles. In such an instance, an offset may be used to account for the difference. The temperature control algorithm may also comprise other offsets to account for other operating conditions that may affect the actual gel temperature as warmed by the medical gel warming system 100.

Use of the medical gel warming system 100 may comprise one or more of the following steps. No defined order of the steps is implied unless specifically stated. The operator may select a desired gel temperature via the operator interface (e.g., pressing a button 106 to select a desired gel temperature). This desired gel temperature may be a preset temperature, a default temperature, or a temperature selected by the operator. The operator may also verify the setting by visually checking the display 105. The operator may open the cover 103, place one or more gel containers (e.g., horizontally) in the warming chamber 108 and close the cover 103. The operator may use the operator interface (e.g., pressing a button 106 or sequence of buttons 106) to change the display 105 to show the current temperature or another parameter. After a specified duration, the operator may again check the current temperature, and if the displayed temperature is within an acceptable range, the operator may remove a gel container and apply at least a portion of the gel in the container to a patient. Thereafter, the operator may return the gel container to the warming chamber 108 or place a separate gel container in the warming chamber 108. The operator may allow the medical gel warming system 100 to be continually operational for several days or more. In other words, there is no need for the medical gel warming system 100 to be turned off, whether or not gel containers are present in the warming chamber 108. The operator may also turn the medical gel warming system 100 off if desired with or without gel containers present in the warming chamber 108. The operator may also adjust the temperature setting at any point when the medical gel warming system 100 is operational. Other steps can also be employed.

References to approximations are made throughout this specification, such as by use of the terms "about." For each such reference, it is to be understood that, in some embodiments, the value, feature, or characteristic may be specified without approximation. For example, where qualifiers such as "about" or "substantially" are used, these terms include within their scope the qualified words in the absence of their qualifiers. All disclosed ranges also include both endpoints.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

What is claimed is:

1. A medical gel warming system comprising:
   a housing;
   one or more chamber walls disposed within the housing and at least partially defining a warming chamber configured to receive one or more containers of gel to be topically applied to a patient;
   a heating element disposed in the housing, the one or more chamber walls being disposed between the heating element and the warming chamber;
   an intermediate thermal coupling member disposed between the heating element and the one or more chamber walls;
   a cover disposed over a top side opening of the warming chamber, the cover configured to selectively 1) allow placement of the one or more containers into the warming chamber and 2) inhibit air flow into and/or out of the warming chamber;
   a temperature sensor disposed within a bottom wall of the one or more chamber walls such that a portion of the bottom wall is disposed between the warming chamber and the temperature sensor; and
   a temperature controller configured to establish and maintain a temperature of the warming chamber as indicated by the temperature sensor.

2. The system of claim 1, wherein the temperature controller is configured to establish and maintain the temperature of the warming chamber at between about 80 and about 105 degrees F.

3. The system of claim 1, wherein the temperature controller is further configured to prevent the temperature of the warming chamber from exceeding a predefined safety limit of 105 degrees F.

4. The system of claim 1, further comprising a display to communicate to a user one or more operating conditions of the medical gel warming system, the one or more operating conditions comprising the current temperature of the warming chamber.

5. The system of claim 1, further comprising an operator interface configured to set or adjust one or more operating parameters of the medical gel warming system, wherein the operating parameters comprise at least a temperature setting.

6. The system of claim 5, wherein the operator interface comprises a plurality of buttons, each button corresponding to a different temperature setting.

7. The system of claim 6, wherein each button, when pressed by the user, defines a temperature setting of between about 95 degrees and about 105 degrees F.

8. The system of claim 6, wherein each button, when pressed by the user, defines a temperature setting previously defined by the user.

9. The system of claim 1, wherein the cover is at least partially translucent or transparent.

10. The system of claim 1, wherein the cover is hingedly coupled to the housing.

11. The system of claim 1, further comprising a power supply electrically coupled to a micro controller, wherein the power supply is at least partially disposed outside the housing.

12. The system of claim 11, wherein the heating element is electrically coupled to the micro controller.

13. The system of claim 12, wherein the heating element extends across at least a bottom wall of the one or more chamber walls.

14. The system of claim 12, wherein the heating element extends upward along one or more side walls of the one or more chamber walls.

15. The system of claim 12, wherein the one or more chamber walls include at least a bottom wall and one or more side walls, and the intermediate thermal coupling member is disposed between the heating element and the one or more side walls and the bottom wall of the one or more chamber walls.

16. A medical gel warming apparatus comprising:
one or more chamber walls defining a warming chamber configured to receive one or more containers of gel;
a cover disposed over a top side opening of the warming chamber, the cover being configured to seal an opening to the warming chamber; and
a temperature controller configured to establish and maintain a temperature of the warming chamber at between about 95 and about 105 degrees F., the temperature controller comprising:
a heating element coupled to the one or more chamber walls;
a temperature sensor configured to measure the temperature of the warming chamber, the temperature sensor disposed within a wall of the one or more chamber walls such that a portion of the wall is disposed between the warming chamber and the temperature sensor;
an intermediate thermal coupling member disposed between the heating element and the one or more chamber walls; and
a micro controller configured to modulate electrical energy applied to the heating element.

17. The apparatus of claim 16, wherein a bottom surface of the one or more chamber walls defining the warming chamber comprises a plurality of protrusions or depressions configured to limit thermal conductance between the bottom surface and the one or more containers of gel.

18. The apparatus of claim 16, wherein the micro controller comprises an algorithm to modulate the electrical energy applied to the heating element.

19. The apparatus of claim 16, wherein the warming chamber is configured to receive one or more bottles of gel in a horizontal orientation, each bottle having a gel capacity of at least eight ounces.

20. A medical gel warming system comprising:
a housing;
one or more chamber walls disposed within the housing and at least partially defining a warming chamber configured to receive one or more containers of gel to be topically applied to a patient;
a heating element disposed in the housing, the one or more chamber walls being disposed between the heating element and the warming chamber;
a cover disposed over a top side opening of the warming chamber, the cover configured to selectively 1) allow placement of the one or more containers into the warming chamber and 2) inhibit air flow into and/or out of the warming chamber;
a temperature sensor disposed within a wall of the one or more chamber walls such that a portion of the wall is disposed between the waarming chamber and the temperature sensor; and
a temperature controller configured to establish and maintain a temperature of the warming chamber as indicated by the temperature sensor.

* * * * *